(12) United States Patent
Goede et al.

(10) Patent No.: US 7,954,492 B2
(45) Date of Patent: *Jun. 7, 2011

(54) PHARMACEUTICAL POWDER CARTRIDGE, AND INHALER EQUIPPED WITH SAME

(75) Inventors: Joachim Goede, Hanau (DE); Martin Herder, Rodgau (DE); Karl-Heinz Lange, Bünde (DE); Meike Eilbracht, Frankfurt (DE)

(73) Assignee: Almirall, S.A., Barcelona (ES)

(*) Notice: Subject to any disclaimer, the term of this patent is extended or adjusted under 35 U.S.C. 154(b) by 382 days.

This patent is subject to a terminal disclaimer.

(21) Appl. No.: 11/270,678

(22) Filed: Nov. 9, 2005

(65) Prior Publication Data

US 2006/0081246 A1    Apr. 20, 2006

Related U.S. Application Data

(62) Division of application No. 10/348,874, filed on Jan. 22, 2003, now Pat. No. 7,258,118.

(60) Provisional application No. 60/351,548, filed on Jan. 24, 2002.

(30) Foreign Application Priority Data

Jan. 24, 2002   (DE) .................................. 102 02 940

(51) Int. Cl.
 *A61M 15/00* (2006.01)
 *A61M 16/00* (2006.01)
(52) U.S. Cl. ................................................. 128/203.19
(58) Field of Classification Search ............. 128/203.15, 128/200.14, 203.12, 209.19, 203.21, 203.23; 604/58

See application file for complete search history.

(56) References Cited

U.S. PATENT DOCUMENTS

| | | | |
|---|---|---|---|
| 2,470,297 A | 5/1949 | Fields | |
| 2,587,215 A | 2/1952 | Priestly | |
| 3,815,754 A | 6/1974 | Rosenberg | |
| 4,184,258 A * | 1/1980 | Barrington et al. | 433/88 |
| 4,274,403 A | 6/1981 | Struve | |
| 4,741,937 A * | 5/1988 | Parker | 428/36.4 |
| 4,899,517 A * | 2/1990 | Shima et al. | 53/432 |
| 5,002,048 A | 3/1991 | Makiej | |
| 5,004,021 A * | 4/1991 | Ulyanitsky et al. | 141/67 |
| 5,007,419 A | 4/1991 | Weinstein et al. | |
| 5,048,514 A | 9/1991 | Ramella | |
| 5,161,524 A * | 11/1992 | Evans | 128/203.15 |

(Continued)

FOREIGN PATENT DOCUMENTS

CA    2316345 A1    7/1999

(Continued)

*Primary Examiner* — Gary Jackson
*Assistant Examiner* — Michael G Mendoza
(74) *Attorney, Agent, or Firm* — Baker & Daniels LLP

(57) ABSTRACT

To improve administration of powdered pharmaceuticals, a pharmaceutical powder cartridge (1) for powder inhalers for holding a pharmaceutical depot for a large number of pharmaceutical powder doses is proposed, having at least one storage space (6) and an integrated metering device, said integrated metering device comprising at least one metering slide (9, 13, 14) which can be moved approximately transversely in a metering slide channel (12) at least from a filling position to an emptying position, approximately transversely with respect to the direction of flow of the pharmaceutical powder out from the at least one storage space (6), said metering slide channel (12) with the at least one metering slide (9, 13, 14) being sealed off from the environment at least in the filling position of the metering slide (9, 13, 14), and also further measures and a corresponding inhaler.

15 Claims, 5 Drawing Sheets

U.S. PATENT DOCUMENTS

| | | | |
|---|---|---|---|
| 5,169,029 A | 12/1992 | Behar et al. | |
| 5,207,217 A | 5/1993 | Cocozza et al. | |
| 5,301,666 A | 4/1994 | Lerk et al. | |
| 5,320,714 A | 6/1994 | Brendel | |
| 5,394,868 A | 3/1995 | Ambrosio et al. | |
| 5,435,301 A | 7/1995 | Herold et al. | |
| 5,441,060 A * | 8/1995 | Rose et al. | 131/271 |
| 5,505,196 A | 4/1996 | Herold et al. | |
| 5,522,380 A | 6/1996 | Dwork | |
| 5,524,613 A | 6/1996 | Haber et al. | |
| 5,544,647 A | 8/1996 | Jewett et al. | |
| 5,603,401 A | 2/1997 | Brunner | |
| 5,664,557 A | 9/1997 | Makiej | |
| 5,687,710 A * | 11/1997 | Ambrosio et al. | 128/203.15 |
| 5,702,362 A | 12/1997 | Herold et al. | |
| 5,769,073 A | 6/1998 | Eason et al. | |
| 5,778,873 A | 7/1998 | Braithwaite | |
| 5,829,434 A | 11/1998 | Ambrosio et al. | |
| 5,840,279 A | 11/1998 | Narodylo et al. | |
| 5,857,457 A | 1/1999 | Hyppola | |
| 5,881,719 A | 3/1999 | Gottenauer et al. | |
| 5,911,937 A * | 6/1999 | Hekal | 264/255 |
| 5,924,417 A | 7/1999 | Braithwaite | |
| 5,947,274 A | 9/1999 | Taskis et al. | |
| 5,964,417 A | 10/1999 | Amann | |
| 6,014,972 A | 1/2000 | Sladek | |
| 6,054,082 A | 4/2000 | Heide | |
| 6,065,471 A | 5/2000 | Schaeffer et al. | |
| 6,071,498 A | 6/2000 | Narodylo et al. | |
| 6,132,394 A | 10/2000 | Lankinen | |
| 6,321,747 B1 | 11/2001 | Dmitrovic et al. | |
| 6,332,461 B1 | 12/2001 | Hyppola | |
| 6,443,152 B1 | 9/2002 | Lockhart et al. | |
| 6,488,648 B1 * | 12/2002 | Matsugi et al. | 604/57 |
| 7,234,464 B2 | 6/2007 | Goede | |
| 7,258,118 B2 | 8/2007 | Goede et al. | |
| 2001/0027789 A1 | 10/2001 | Goede et al. | |
| 2003/0005926 A1 | 1/2003 | Jones et al. | |
| 2004/0056054 A1 | 3/2004 | Ottolangui | |

FOREIGN PATENT DOCUMENTS

| | | |
|---|---|---|
| CA | 2324524 A1 | 9/1999 |
| CA | 2411109 A1 | 12/2001 |
| CA | 2090227 C | 11/2004 |
| DE | 846770 C | 8/1952 |
| DE | 3535561 A1 | 5/1986 |
| DE | 4400083 A1 | 7/1995 |
| DE | 4400084 A1 | 7/1995 |
| DE | 4436854 A1 | 4/1996 |
| DE | 19523516 C1 | 10/1996 |
| DE | 195 22 415 A1 | 1/1997 |
| DE | 19522416 A1 | 1/1997 |
| DE | 19647947 A1 | 5/1998 |
| DE | 19757208 A1 | 6/1999 |
| EP | 0416950 A1 | 3/1991 |
| EP | 0416951 A1 | 3/1991 |
| EP | 0640354 A2 | 3/1995 |
| GB | 2165159 A | 4/1986 |
| JP | 9301400 A | 11/1997 |
| JP | 10-511594 T | 11/1998 |
| MX | PA02005279 A | 9/2003 |
| PL | 182198 B1 | 11/2001 |
| RU | 2162346 C2 | 1/2001 |
| WO | WO92/03175 A1 | 3/1992 |
| WO | WO92/09322 A1 | 6/1992 |
| WO | WO93/11773 A1 | 6/1993 |
| WO | WO93/16748 A2 | 9/1993 |
| WO | WO 95/31237 | 11/1995 |
| WO | WO97/00703 A1 | 1/1997 |
| WO | WO99/47195 A1 | 9/1999 |
| WO | WO00/64519 A1 | 11/2000 |
| WO | WO00/74754 A2 | 12/2000 |
| WO | WO01/21238 A2 | 3/2001 |
| WO | WO01/39823 A1 | 6/2001 |
| WO | WO 01/41849 | 6/2001 |
| WO | WO 01/43800 | 6/2001 |
| WO | WO01/46038 A1 | 6/2001 |
| WO | WO02/49569 A2 | 6/2002 |
| ZA | 9106741 A | 5/1992 |

* cited by examiner

PHARMACEUTICAL POWDER CARTRIDGE, AND INHALER EQUIPPED WITH SAME

CROSS-REFERENCE TO RELATED APPLICATIONS

This is a Divisional of U.S. patent application Ser. No. 10/348,874 now U.S. Pat. No. 7,258,118 filed Jan. 22, 2003, which is a non-provisional of U.S. Provisional Patent Application Ser. No. 60/351,548, filed on Jan. 24, 2002, the disclosures of which are both hereby expressly incorporated by reference herein.

The invention relates to a pharmaceutical powder cartridge for powder inhalers for holding a pharmaceutical depot for a large number of pharmaceutical powder doses, having at least one storage space and an integrated metering device, said integrated metering device comprising at least one metering slide which can be moved approximately transversely in a metering slide channel at least from a filling position to an emptying position, approximately transversely with respect to the direction of flow of the pharmaceutical powder out from the at least one storage space, and an inhaler equipped accordingly.

BACKGROUND OF THE INVENTION

In the field of treatment of bronchial diseases, and also of other diseases in which medication can be given via the airways, it is known not only to atomize solutions or suspensions into inhalable aerosols but also to administer powdered medicaments. Many examples of such medicaments are described in the literature, and of these we refer purely by way of illustration to WO 93/11773, EP 0 416 950 A1 and EP 0 416 951 A1.

A customary form of administration in this connection is delivery via an inhalation device (inhaler).

Known inhalers for powdered pharmaceuticals include those for administration of a single dose and also inhalation devices which have a storage space for a plurality of pharmaceutical doses. In connection with the latter, it is known either to provide separate storage spaces for each individual dose or to provide one single receiving space for receiving a multiplicity of doses of a medicament.

Known inhalers in which a large number of individual doses are provided in separate storage spaces include those in which individual areas of the inhaler are each filled with a pharmaceutical dose. An example of such an inhaler is described in U.S. Pat. No. 5,301,666 A. However, it is also known to accommodate a large number of pharmaceutical powder doses in separate areas of what are called blister packs. An example of such a blister pack for use with an inhaler is described in DE 44 00 083 C2. Such a blister pack, which is designed at the same time as a disposable inhaler, is described for example in DE 44 00 084 A1.

An inhalation device into which blister packs can be inserted, which each have separate storage spaces for individual doses of a powdered pharmaceutical and which can be emptied one after another with the aid of the inhalation device, is described, for example, in DE 195 23 516 C1.

Many examples of inhalers with a storage space for a large number of pharmaceutical doses are described in the prior art. One example with an exchangeable storage container is described in German Patent Specification 846 770, and another in WO 95/31237.

An important problem with inhalation systems in which a large number of doses of a medically active substance are accommodated in a common storage space concerns the apportioning of an individual dose for one individual inhalation. In this connection, a great many solutions have been proposed, for example those which are described in U.S. Pat. No. 2,587,215 A and U.S. Pat. No. 4,274,403 A. Other types of arrangements for metering an individual dose of pharmaceutical powder from a storage space for a large number of pharmaceutical doses are furthermore described in WO 92/09322, WO 93/16748 and DE 35 35 561 C2 and in GB 2 165 159 A. An exchangeable cartridge for receiving a large number of doses of a pharmaceutical powder with an integrated metering slide is known from DE 195 22 415 A1.

Another important problem with inhalation of pharmaceutical powders concerns the breakdown of the galenic powder formulations into particles which can access the lungs. The active substances administered in this way are generally combined with vehicles in order to achieve a reasonable dosing capacity of the medically active substance and to set further properties of the pharmaceutical powder, which for example can influence the storage life.

Proposed solutions concerning the designs of powder inhalers with which particles which can access the lungs are intended to be made available in an air stream for inhalation are described for example in EP 0 640 354 A2, U.S. Pat. No. 5,505,196 A, U.S. Pat. No. 5,320,714 A, U.S. Pat. No. 5,435, 301 A, U.S. Pat. No. 5,301,666 A, DE 195 22 416 A1 and WO 97/00703. Proposals are also known to use auxiliary energy to generate the air stream, for example in ZA-A 916741.

In the use of medicaments for inhalation in powder form, it is also quite generally known to combine active substances by administering prepared active substance mixtures. Corresponding proposals are found in EP 0 416 951 A1 and WO 93/11773, for example for combination of salmeterol and fluticasone or formoterol and budesonide.

WO 00/74754 and many other publications over a period of more than twenty years have described how, particularly in powder inhalers, there is a considerable problem with moisture. Not only can moisture have a disadvantageous effect on the pharmaceutically active composition of the medicament, it can also impair in particular the interplay of physical and chemical parameters of the combination of active substance and auxiliaries. As a result, lumps may form, for example, or the breakdown of the inhaled powder into particles which can access the lungs may be impaired. All these circumstances can lead to problems affecting the metering and the efficacy of the administration of a powdered medicament.

To minimize these disadvantages, various attempts have already been made in the past to reduce the penetration of moisture into a powder inhaler by using seals. Attempts have also been made to reduce the disadvantageous effects of penetrated moisture by providing desiccants to absorb the moisture, in particular to keep the air moisture in storage chambers to a minimum.

PRIOR ART

In the prior art, WO 00/74754 expressly describes how attempts to solve this problem have generally been made only by the use of desiccants in various forms. The Applicant there claims to have solved this problem by for the first time providing a seal intended to prevent penetration of moisture into the inhaler, particularly into the storage container of a powder inhaler with in particular elastic sealing elements.

To this end, reference is made to sealing elements made from "all conventionally known materials, for example natural or synthetic rubber, a silicone or PTFE" and like materials.

Subsequently, with reference to the "Clickhaler" powder inhaler from Innovata Biomed, an arrangement is described in detail which concerns a particular arrangement of the metering mechanism of this inhaler, which comprises a metering device in the manner of a star feeder in the form of an inclined truncated cone.

In the embodiment described, the sealing element provided is a likewise frustoconical sealing sleeve which is fitted over the truncated metering cone and is intended to be pivotable, so that it can assume a sealing position and a non-sealing position. Here, page 5 interestingly describes how this sealing sleeve is preferably to be made of a synthetic material like that of the metering cone. It is further proposed that the sealing sleeve be provided with the same number of holes as the metering cone element has metering cavities. The sealing sleeve and the metering element are to be designed in such a way that, when both are turned, a metering chamber formed by an opening in the sealing sleeve first takes up the medicament from the reservoir and then, upon further turning, deposits this in the metering cavity in the actual metering cone and is finally conveyed from there into an air channel.

A particularly advantageous embodiment is described in which the outer contour of the sealing sleeve forms a spherical section and provides a good fit with a corresponding curvature of the medicament storage space. The inner contour of the sealing sleeve is intended to be adapted to the frustum of the metering cone.

From U.S. Pat. No. 6,132,394 A, it is known to provide, in a medicament chamber of an inhaler, a separate container containing a desiccant. This is described as differing from U.S. Pat. No. 4,274,403 A in that a completely closed separate container is used which is made of a material which is as far as possible permeable to moisture and in which the desiccant, for example silica gel, is to be placed. An important advantage of this is stated to be the fact that, compared to conventional dry capsules, there are no assembly or connection points through which small amounts of the desiccant can pass into the medicament chamber and thus contaminate the powdered medicament. In conventional dry capsules, such connection points are to be present in particular between capsule body and porous membrane through which the water vapour is to pass into the desiccant.

The separate container is accordingly intended to be made as far as possible from a single material, preferably one with a high degree of water vapour permeability. Suitable materials proposed are polycarbonate (PC) and ABS (acrylonitrile-butadiene-styrene). The drying behaviour over a relatively long period of time is intended here to be adapted via the material of the container.

WO 01/46038 discloses the use of a stopper, a foil, a tablet or a lining of an EVA copolymer with 35-80% by weight of a desiccant such as silica gel, clay or zinc chloride as desiccant capsule or embedded in a storage container in particular for packaged foods, mention being made of deficient mechanical stability of the stopper etc., and the risk of mechanical decomposition at relatively high concentrations of desiccant. Here, the EVA types described as being suitable have quite high proportions of vinyl acetate copolymers, so that these materials have very high water vapour permeability.

WO 01/21238 discloses a powder inhaler with hermetic sealing when not in use. To this end, in the case of a powder inhaler with a medicament storage space and with an air channel running through under the storage space, a sealing skirt is provided on each side of the storage container and covers an air inlet opening and an inhalation opening of the air channel in a position of rest. When an actuating cap is actuated to move a metering plunger through the storage space in order to convey a dose of medicament from the reservoir into the air channel, the two sealing skirts secured on the actuating cap are moved downwards too until the metering plunger has reached its emptying position. Through-holes are provided in the sealing skirts and are arranged in such a way that, with the actuating cap in the end position, they free the openings of the air channel. As long as the actuating cap is kept depressed, the air can be sucked through the air channel. When the actuating cap is released and returns to its starting position, the openings of the air channel are closed again.

By means of an additional guide arrangement and an elastic design of the sealing skirts, these are pressed against the outer wall in order to increase the sealing effect. In this arrangement, as the distance travelled from the opening position to the closing position increases, the sealing skirts are pressed increasingly more strongly against the outer wall of the inhaler transverse to the direction of movement. An elastic seal in the form of a bellows is also provided between actuating cap and inhaler housing in order to close the gap between said structural parts.

SUMMARY OF THE INVENTION

The object of the invention is therefore to improve known systems for administering powdered pharmaceuticals.

According to the invention, this object is achieved by means of a pharmaceutical powder cartridge for powder inhalers for holding a pharmaceutical depot for a large number of pharmaceutical powder doses, having at least one storage space and an integrated metering device, said integrated metering device comprising at least one metering slide which can be moved approximately transversely in a metering slide channel at least from a filling position to an emptying position, approximately transversely with respect to the direction of flow of the pharmaceutical powder out from the at least one storage space, the metering slide channel with the at least one metering slide being sealed off from the environment at least in the filling position of the metering slide.

By means of the design according to the invention, and for only the slightest additional outlay, an effective protection of the pharmaceutical storage space against moisture from the environment is obtained, in particular during intermediate storage during the period of use after the patient has begun using the storage space. This advantage applies both while the pharmaceutical cartridge is fitted in an inhaler and also when it is being stored outside the inhaler. Compatibility with known powder inhalers for exchangeable pharmaceutical powder cartridges of the type mentioned at the outset can be maintained.

In a particularly preferred embodiment, a pharmaceutical powder cartridge according to the invention is characterized in that the metering slide channel has, at one end, an opening to the environment through which a part of the metering slide can pass, and, around the opening, a contact surface is provided for a seal.

A particularly reliable function can be achieved if the metering slide has a sealing surface provided in a plane approximately transverse to its direction of movement from the filling position to the emptying position. In this way, it is at the same time possible to avoid a change of frictional forces during the movement of the metering slide which, in known inhalers, can be caused by a movement of the seal along the sealing surface, by powder residues or wear of the seal.

Particularly reliable sealing is achieved if said sealing is provided by an elastic seal.

In the case of prolonged storage prior to the pharmaceutical powder cartridge being inserted into an inhaler, an especially permanent and effective sealing is guaranteed if the metering slide can further be moved into an additional storing position and the seal is elastically prestressed sealingly at least in the storing position of the metering slide, especially if the metering slide is fixed in the storing position by resiliently elastic means.

In a preferred embodiment, a pharmaceutical powder cartridge according to the invention is characterized in that the metering device comprises at least one metering cavity for holding a predetermined quantity of a pharmaceutical powder.

For administering active substance combinations, it can also be advantageous if the pharmaceutical powder cartridge has at least two storage spaces, in particular if the pharmaceutical powder cartridge has a metering device, said metering device having, for each of the storage spaces, a metering cavity for apportioning a predetermined quantity of each medically active substance provided in the storage spaces. Depending on the active substance combination provided, it is also advantageous if the metering devices of the individual pharmaceutical powder cartridges have metering cavities of identical or different volume.

A particularly economical application, especially suitable for expensive pharmaceutical powders with only occasional administration, is possible if the pharmaceutical powder cartridge further has a device for indicating the quantity of pharmaceutical doses which remain in the storage chambers or which have been removed from the storage chambers.

The advantages of the invention can be used especially in long-term use of a pharmaceutical powder cartridge for powder inhalers for holding a pharmaceutical depot for a large number of pharmaceutical powder doses, having at least one storage space and an integrated metering device, said integrated metering device being able to assume at least a filling position and an emptying position and being able to move from the filling position to the emptying position, and with a seal being provided which substantially seals off the storage space from the environment and against entry of moisture, at least in the filling position of the metering device, said seal being elastically deformable, during a movement of the metering device from its emptying position to its filling position, without any sliding movement of the seal relative to the sealing surfaces.

In a preferred embodiment of the invention, the seal is made of a silicone rubber or an elastomer, more preferably a thermoplastic elastomer, preferably of TPEE (thermoplastic polyester elastomer).

The improvement in the application properties afforded by the invention, particularly through actively reducing the effect of moisture on a pharmaceutical powder during the period of use by a patient or a hospital establishment, is further achieved by means of a pharmaceutical powder cartridge for powder inhalers or a powder inhaler having at least one storage space for holding a pharmaceutical depot for a large number of pharmaceutical powder doses, including a housing body and a lid which substantially enclose the at least one storage space, and where the housing body and/or the lid are made predominantly of a PVDC (polyvinylidene chloride), a pharmaceutically compatible plastic coated completely or partially with PVDC, an olefin copolymer with heterocyclic side groups (COC or mPP), or a PCTFE (polychloro-trifluoroethylene).

In a particularly advantageous embodiment, a pharmaceutical powder cartridge according to the invention is characterized in that at least one metering slide as a component of the metering device is made predominantly of a PVDC (polyvinylidene chloride), a pharmaceutically compatible plastic coated completely or partially with PVDC, an olefin copolymer with heterocyclic side groups, an at least partially oriented PP (polypropylene) or a PCTFE (polychloro-trifluoroethylene).

To limit the effects of moisture, which has penetrated into the cartridge or is present therein, on a pharmaceutical powder, it is further expedient if a pharmaceutical powder cartridge for powder inhalers or a powder inhaler according to the invention is characterized in that the housing body and/or lid comprises, on at least part of the side facing the storage space, a blend of desiccant embedded in a thermoplastic matrix.

To avoid impairment of the pharmaceutical by desiccant residues, it is advantageous, according to the invention, to provide a pharmaceutical powder cartridge for powder inhalers or a powder inhaler having at least one storage space for holding a pharmaceutical powder depot for a large number of pharmaceutical doses, containing at least one shaped body made of a blend of a thermoplastic matrix with a desiccant embedded therein, preferably silica gel, bentonite or molecular sieve, particularly if channels are formed in a matrix of a thermoplastic of low water absorption, as are obtainable by dissolving soluble co-extrudate components. For rapid uptake of residual moisture in the storage space, it can also be expedient in this case if fibres which absorb water vapour are embedded as filler in a matrix of a thermoplastic of low water absorption.

It is particularly advantageous, for economic mass production, if the blend in a matrix of a thermoplastic of low water absorption and a desiccant embedded therein is designed at least as part of an inner wall of a storage space by multi-component injection-moulding in a housing body made of a plastic substantially impermeable to water vapour.

Within the meaning of the invention, it is further advantageous if housing body and lid are sealed watertight, preferably by ultrasonic welding.

For particularly economic production, the seal is co-injected onto the housing body or the metering slide.

The invention can be advantageously exploited in economic terms using an inhaler for powdered pharmaceuticals with a pharmaceutical powder cartridge according to the invention, and with an inhaler for powdered pharmaceuticals, in which the pharmaceutical can be taken by a patient by way of an air stream, characterized by a holder for a pharmaceutical powder cartridge according to the invention.

The advantages of the invention are particularly beneficial for patients requiring treatment with a pharmaceutical powder cartridge according to the invention containing a powder with one or more of the following active substances: analgesics, anti-allergics, antibiotics, anticholinergics, anti-histamines, anti-inflammatory substances, antipyretics, corticoids, steroids, antitussives, bronchodilators, diuretics, enzymes, substances acting on the cardiovascular system, hormones, proteins and peptides.

APPLICATION OF THE INVENTION

By means of the invention, it is possible to make available pharmacodynamically active substances in the form of powdered pharmaceuticals over a long period of use, even when they are sensitive to moisture or are under unfavourable climatic conditions, and in so doing also to obtain the advantages of re-usable inhalers with exchangeable pharmaceutical powder cartridges.

It is also possible to make available powdered pharmaceuticals for inhalation in different active substance combinations under improved storage conditions, of which individual active substances have increased sensitivity to moisture affecting their storage life, their stability or their dosability. Active substances for which the invention can be used can also be for example from the group of beta-sympathomimetics: salbutamol, reproterol, fenoterol, formoterol, salmeterol. Possible examples from the group of corticosteroids are: budesonide, beclomethasone, fluticasone, triamcinolone, loteprednol, mometasone, flunisolide, ciclosonide. Possible examples from the group of anticholinergics are: ipatropium bromide, thiotropium bromide, glycopyrrolate.

Possible examples from the group of analgesics and anti-migraines are: morphine, tramadol, flupirtine, sumatryptan. The following can be used for example from the group of peptides and proteins: cetrorelix, insulin, calcitonin, parathyroid hormone, factor VIII analogs, interferon alpha, interferon beta, heparin, FSH (follicle-stimulating hormone), colistin, tobramycin.

Use is not limited to the active substances mentioned here. The pharmaceutical powder cartridge described is suitable for all active substances which can be metered in powder form and administered by inhalation. By appropriate modification of the system and of the metering device, the invention described is also suitable for combination of active substances which contain liquid formulations, for example solutions or suspensions of pharmacodynamically active substances.

Pharmaceutical powder formulations which can expediently be used with the pharmaceutical powder cartridge system according to the invention can contain various active substances, such as, for example, analgesics, anti-allergics, antibiotics, anticholinergics, antihistamines, anti-inflammatory substances, antipyretics, corticoids, steroids, antitussives, bronchodilators, diuretics, enzymes, cardiovascular agents, hormones, proteins and peptides. Examples of analgesics are codeine, diamorphine, dihydromorphine, ergotamine, fentanyl and morphine; examples of anti-allergics are cromoglycinic acid and nedocromil; examples of antibiotics are cephalosporins, fusafungine, neomycin, penicillins, pentamidine, streptomycin, sulphonamides and tetracyclines, colistin, tobramycin; examples of anticholinergics are atropine, atropine methonitrate, ipratropium bromide, oxitropium bromide, trospium chloride and thiotropium bromide; examples of antihistamines are azelastine, flezelastine and methapyrilene; examples of anti-inflammatory substances are beclomethasone, budesonide, loteprednol, dexamethasone, flunisolide, fluticasone, tipredane, triamcinolone, mometasone; examples of antitussives are narcotine and noscapine; examples of bronchodilators are bambuterol, bitolterol, carbuterol, clenbuterol, ephedrine, epinephrine, formoterol, fenoterol, hexoprenaline, ibuterol, isoprenaline, isoproterenol, metaproterenol, orciprenaline, phenylephrine, phenylpropanolamine, pirbuterol, procaterol, reproterol, rimiterol, salbutamol, salmeterol, sulfonterol, terbutaline and tolobuterol; examples of diuretics are amiloride and furosemide; an example of an enzyme is trypsin; examples of cardiovascular agents are diltiazem and nitroglycerin; examples of hormones are cortisone, hydrocortisone and prednisolone; examples of proteins and peptides are cyclosporine, cetrorelix, glucagon and insulin. Further active substances which can be used are adrenochrome, colchicine, heparin, scopolamine. The active substances listed by way of example can be used as free bases or acids or as pharmaceutically acceptable salts. Counterions which can be used include, for example, physiological alkaline earth metals or alkali metals or amines, for example acetate, benzene sulphonate, benzoate, hydrogen carbonate, hydrogen tartrate, bromide, chloride, iodide, carbonate, citrate, fumarate, malate, maleate, cluconate, lactate, pamoate and sulphate. Esters can also be used, for example acetate, acetonide, propionate, dipropionate, valerate.

The invention also allows the doctor to very accurately adapt the dose to the patient over a long period of time, without the need to dispose of partially emptied cartridges, which would have a disadvantageous effect on treatment costs, and without compromising compatibility with other cartridges with different metering devices, e.g. with the cartridge known from WO 97/00703.

DESCRIPTION OF PREFERRED ILLUSTRATIVE EMBODIMENTS

Figure 1:
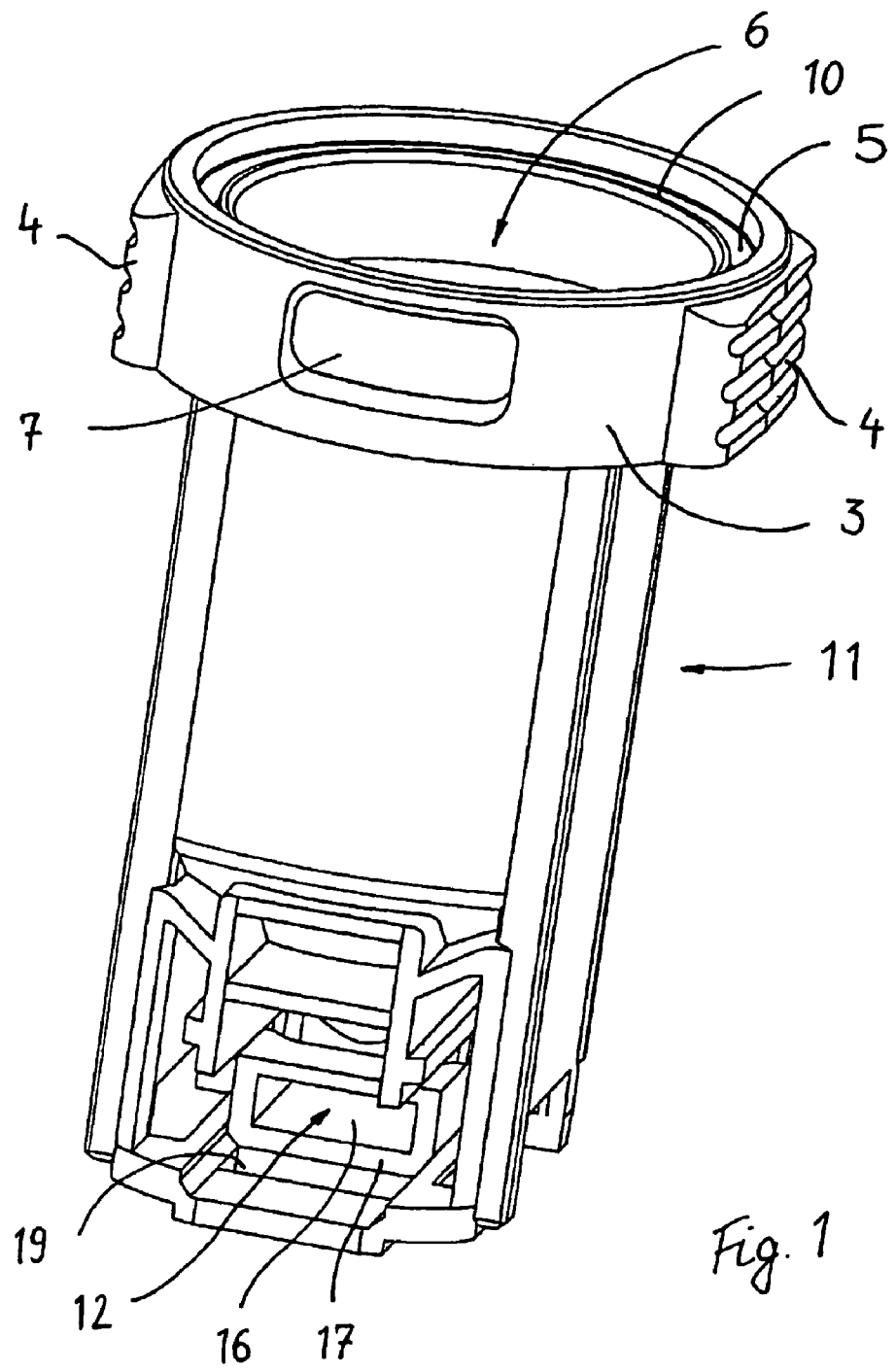
FIG. 1 shows a pharmaceutical powder cartridge according to the invention, in a perspective view.

FIG. 1 shows a perspective view of a housing body 11 of a pharmaceutical powder cartridge 1 according to the invention for exchangeable insertion into a powder inhaler 2. The pharmaceutical powder cartridge 1 shown here has, at the upper area of its housing body 11, an edge 3 which includes two grip areas 4 in order to permit easy insertion of the pharmaceutical powder cartridge 1 into a powder inhaler 2. In the illustrative embodiment shown, a device for indicating the amount of pharmaceutical doses which remain in the storage space 6 or have been removed from the storage space 6 is provided at the same time in the edge 3, in an annular channel 5 formed therein (the device is not shown in detail however), for example in the form of foil strips with corresponding markings as is described in detail in WO 97/00703. The user can then read off the markings through the viewing window 7 in the edge 3.

The edge 3 also serves to receive a lid 8 with which the storage space 6 forming the main part of the pharmaceutical powder cartridge 1 can be sealed off. Such a lid 8 is expediently sealed in a watertight manner to a collar 10 formed within the edge 3, for example by ultrasonic welding.

Figure 2:
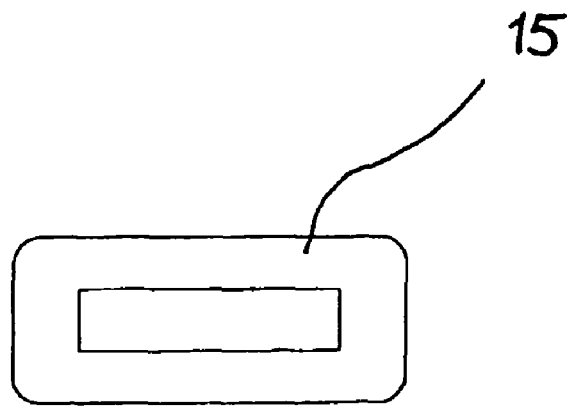
FIG. 2 shows a plan view of a seal of a pharmaceutical powder cartridge according to the invention.
Figure 3:
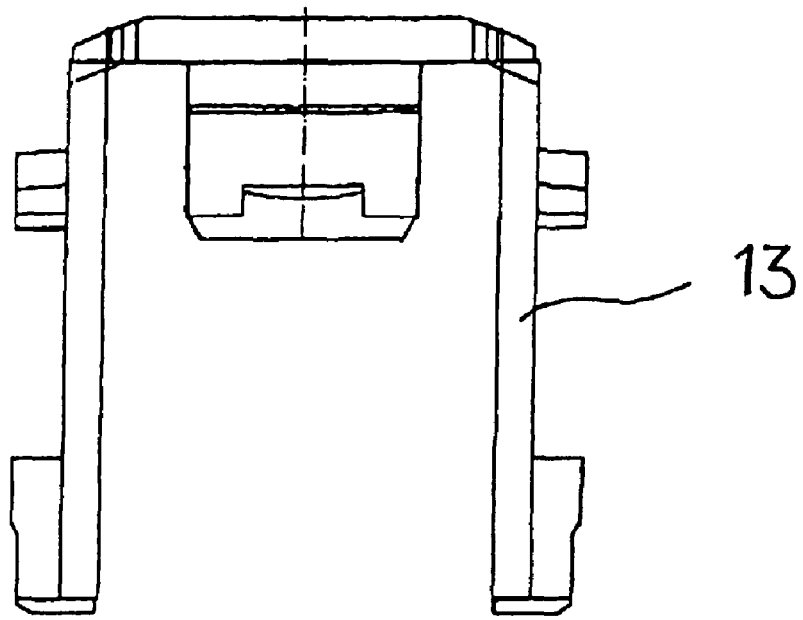
FIG. 3 shows a view of a carrier mechanism of a metering slide in a pharmaceutical powder cartridge according to the invention.

Arranged below the storage space 6 there is a metering slide channel 12 in which a metering slide acting as metering device is movably arranged, which metering slide, in the illustrative embodiment described here, is made up of three parts, namely a carrier 13, the actual metering slide body 14, and a seal 15 (FIGS. 2, 3, 4A and 4B). The metering slide is configured in such a way that the seal 15 shown in FIG. 2 is inserted into the carrier 13 shown in FIG. 3 and the carrier 13 is clipped with seal 15 onto the metering slide body 14.

Figure 5:
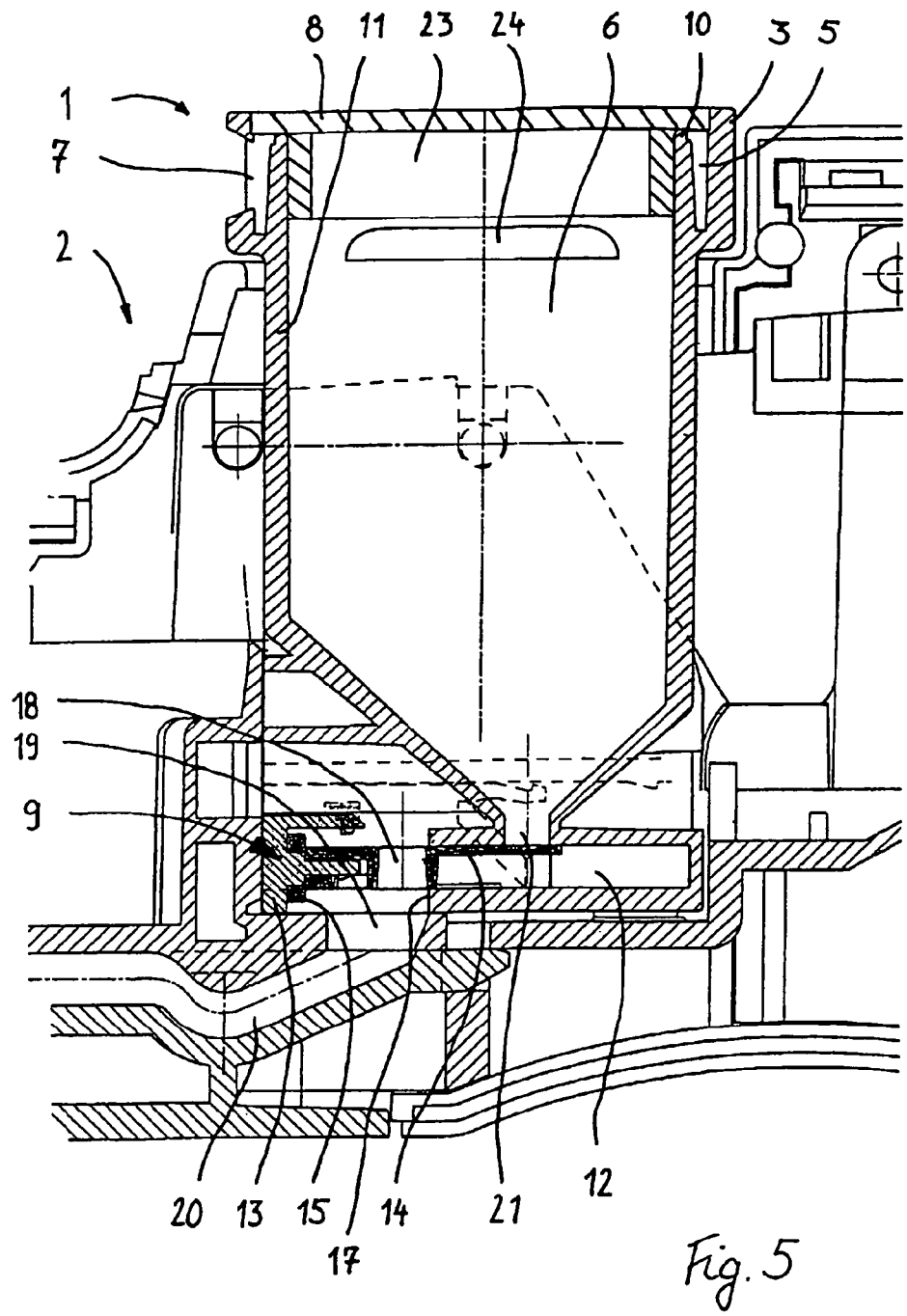
FIG. 5 shows a longitudinal section through a pharmaceutical powder cartridge according to the invention, in an inhaler with the metering slide in the emptying position.
Figure 6:
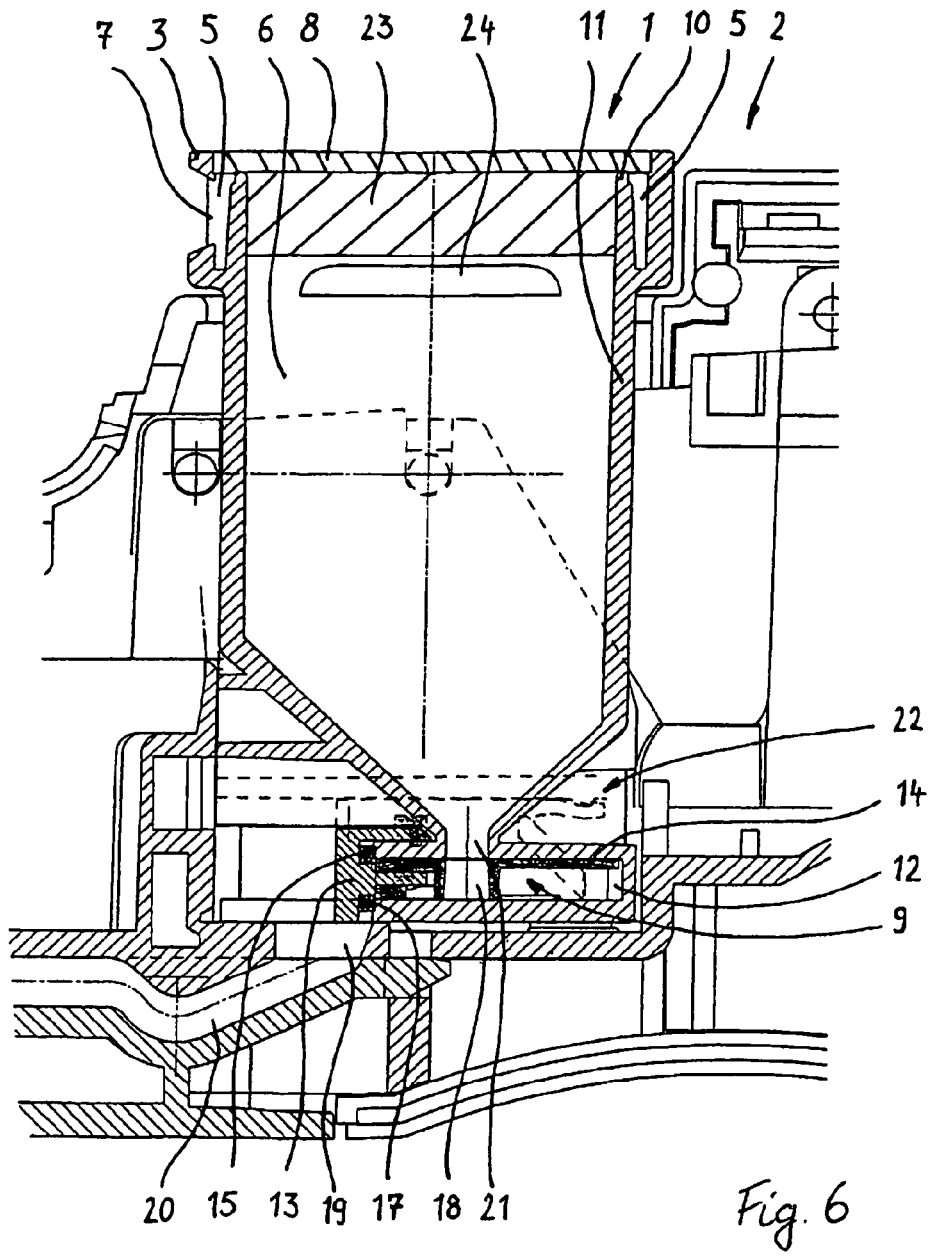
FIG. 6 shows a longitudinal section through a pharmaceutical powder cartridge according to the invention, in an inhaler with the metering slide in the filling position.

As can be clearly seen from FIG. 1, the metering slide channel 12 at one end has an opening 16 and, formed around the opening 16, there is a contact surface 17 for the seal 15 of the metering slide. The contact surface 17 is at the same time provided as a sealing surface and extends in a plane approximately perpendicular to the direction of movement of the metering slide from a filling position, as is shown in FIG. 6, to an emptying position, as is shown in FIG. 5.

Figure 4B:
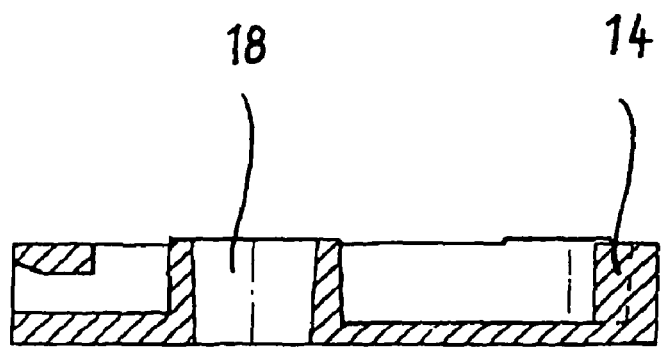
FIG. 4B shows a longitudinal section through the metering slide body of a pharmaceutical powder cartridge according to the invention from FIG. 4A.
Figure 4A:
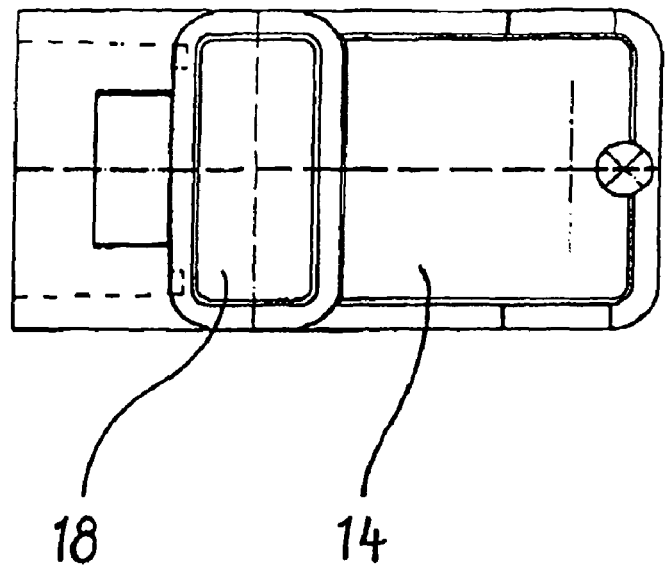
FIG. 4A shows a view of a metering slide body in a pharmaceutical powder cartridge according to the invention.

The metering slide body 14 shown in FIGS. 4A and 4B comprises a metering cavity 18 whose holding volume represents the dose quantity to be made available for an inhalation. The seal 15 can for example be co-injected in multi-component injection-moulding and for this purpose can be made, for example, of a thermoplastic elastomer.

Correspondingly, a sealing surface can be provided on the metering slide and the elastic seal 15 can be mounted or better still injection-moulded in the area of the opening 16 of the metering slide channel 12.

The housing body 11 and/or the lid 8 and/or the metering slide body 14 can advantageously be made of a COC by injection-moulding. A suitable material with the name TOPAS® 8007 is commercially available as a trial product from the company Ticona in Germany.

For pharmaceutical combinations in which the powders cannot be stored, or cannot adequately be stored, as a mixture, it can also be expedient to provide two storage chambers instead of the one storage-space 6.

FIGS. 5 and 6 show a longitudinal section through the pharmaceutical powder cartridge 1 inserted into an inhaler 2. As can be seen from the figures, the metering slide, designated overall by 9, can move in the metering slide channel 12 at least from the filling position shown in FIG. 6 to the emptying position shown in FIG. 5.

In the filling position shown in FIG. 6, pharmaceutical powder can fall from the storage space 6 into the metering cavity 18. When the metering cavity 18 has been filled, as desired, with a pharmaceutical powder, the metering slide 9 can be moved to the emptying position shown in FIG. 5 with the aid of engagement means in a powder inhaler which are only indicated schematically here, for example such as those described in U.S. Pat. No. 5,840,279 A, and which cooperate with the carrier 13.

The emptying position is reached when the metering cavity 18 is situated over an emptying opening 19. When the metering slide 9 has reached this position, the pharmaceutical powder can fall from the metering cavity 18 through the emptying opening 19, for example into a powder channel 20 of an inhaler 2.

The filling position of the metering slide 9 can be seen clearly in FIG. 6, with the metering cavity 18 under a hole 21 on the underside of the storage space 6. To reach the empting position, the metering slide 9 is pushed to the left in FIG. 6 until this metering cavity 18 covers the emptying opening 19 and the pharmaceutical powder can fall down from it.

It can also be clearly seen in FIG. 6 that the seal 15 of the metering slide 9 lies on the contact surface 17 of the metering slide channel 12 and ensures a good sealing, preferably with slight elastic deformation. This can be done by prestressing with resiliently elastic means, in particular via an actuating device in the inhaler for the metering slide 9, which expediently also effects an immediate reverse movement of the metering slide 9 from the emptying position, as shown in FIG. 5, to its sealed filling position, as shown in FIG. 6, as soon as a pharmaceutical dose has been removed.

For a higher contact pressure of the seal 15 of the metering slide 9 on the contact surface 17 of the metering slide channel 12, and thus for a particularly reliable sealing during storage of a pharmaceutical powder cartridge according to the invention, especially prior to its first use in a powder inhaler, it is advantageous to provide, slightly further to the right in the view in FIG. 6, an additional storing position for the metering slide 9 of a filled pharmaceutical powder cartridge 1 in which the metering slide 9 can be fixed by the releasable snap connection 22 shown. In this storing position, the seal 15 of the metering slide 9 on the contact surface 17 of the metering slide channel 12 is subject to an increased prestressing force.

In the upper area of the storage space there is also advantageously a shaped body 23 which is preferably secured in its position via corresponding shaped edges 24, in order to avoid mechanical loading of the pharmaceutical powder. The shaped body 23 is expediently produced by injection-moulding from a blend of a thermoplastic matrix and a desiccant. The desiccant is intended in particular to absorb moisture which is situated in the storage space 6 or which has penetrated through the metering cavity 18. The use of such a shaped body 23 ensures that no crumbs of the desiccant, typically silica gel, can pass into the pharmaceutical powder and thus into the airways of a patient. Such a shaped body can be made of a PP matrix which itself does not take up water and which is injected mixed with a water-soluble compound and the desiccant, for example polyethylene glycol, and the water-soluble compound is then washed out. This results in a sponge-like structure with channels which, after the shaped body has dried, permit rapid water absorption of the (not water-soluble) silica gel through large surfaces using capillary condensation.

In order to obtain a rapid water absorption in the whole shaped body 23, it may also be expedient to embed suitable fibres as filler in the blend of desiccant and thermoplastic matrix, which fibres, by means of their capillary action, ensure rapid transport of the air moisture and of the water to the desiccant.

The shaped body 23 can also be designed in the form of a wall lining in the manner of an insert, as is shown purely by way of example in FIG. 5, or, by multi-component injection-moulding in the production of the pharmaceutical powder cartridge, can form all or part of an inner wall of the storage space 6.

The invention claimed is:

1. A pharmaceutical powder cartridge removably insertable into a powder inhaler, said cartridge having a storage space defining a pharmaceutical depot for holding a large number of pharmaceutical powder doses, said cartridge including a housing body defining said storage space and a lid for substantially enclosing said storage space, said cartridge further including a metering device, said metering device including a metering slide channel and a metering slide received within said metering slide channel and defining a dosing cavity, said metering slide movable within said metering slide channel between a filling position in which said dosing cavity of said metering slide is in communication with said storage space and a dispensing position in which said dosing cavity of said metering slide is not in communication with said storage space, said cartridge further including a single elastic seal member, said seal separate from and in abutment with said metering slide, said seal member preventing moisture from the environment from entering the storage space when the metering slide is in said filling position;

wherein said metering slide channel is defined by a pair of opposing parallel walls and said metering slide is received between and slidable with respect to said walls, and said seal member engages said pair of opposing parallel walls when said metering slide is in said filling position and does not engage said pair of opposing parallel walls when said metering slide is in said dispensing position.

2. The cartridge of claim 1, in combination with at least one powdered pharmaceutical contained within said storage space.

3. The cartridge of claim 1, wherein said lid is permanently_secured to said housing body.

4. The cartridge of claim 1, wherein said metering device further comprises a sealing member, said sealing member in engagement with said housing when said metering device is in said filling position.

5. The cartridge of claim 4, wherein said metering device further comprises a latch member initially retaining said metering device in said filling position with said sealing member in engagement with said housing.

6. The cartridge of claim 1, wherein at least one of said housing body and said lid made predominantly from one of a polyvinylidene chloride, a pharmaceutically compatible plastic coated completely or partially with polyvinylidene chloride, an olefin copolymer with heterocyclic side groups, and a polychlorotrifluoroethylene.

7. The cartridge of claim 1, wherein said metering slide is linearly movable in a direction transverse to a longitudinal axis of said cartridge.

8. The cartridge of claim 1, wherein said seal member is an annular member.

9. A pharmaceutical powder cartridge removably insertable into a powder inhaler, said cartridge having a storage space for holding a pharmaceutical depot for storing a large number of pharmaceutical powder doses, said cartridge having a shaped body made from a porous matrix of an injection-molded blend of a thermoplastic and a silica gel desiccant, said silica gel desiccant embedded within said matrix, said cartridge having a hole on the underside of said storage space for delivering the pharmaceutical powder from within the storage space, said cartridge further including a separate single elastic seal member, said seal member separate from said body and said storage space and disposed beneath said underside of said storage space, said seal member preventing moisture from the environment from entering the storage space through the hole;

wherein said metering slide channel is defined by a pair of opposing parallel walls and said metering slide is received between and slidable with respect to said walls, and said seal member engages said pair of opposing parallel walls when said metering slide is in said filling position and does not engage said pair of opposing parallel walls when said metering slide is in said dispensing position.

10. The cartridge of claim 9, in combination with at least one powdered pharmaceutical contained within said storage space.

11. The cartridge of claim 9, further comprising a lid, said lid permanently secured to a housing body of said cartridge.

12. The cartridge of claim 9, wherein said body further includes a metering device, said metering device including a metering slide channel and a metering slide received within said metering slide channel and defining a dosing cavity, said metering slide movable within said metering slide channel between a filling position in which said dosing cavity of said metering slide is in communication with said storage space and a dispensing position in which said dosing cavity of said metering slide is not in communication with said storage space.

13. The cartridge of claim 12, wherein said metering device further comprises a sealing member, said sealing member in engagement with said housing when said metering device is in said filling position.

14. The cartridge of claim 13, wherein said metering device further comprises a latch member initially retaining said metering device in said filling position with said sealing member in engagement with said housing.

15. The cartridge of claim 9, wherein said seal member is an annular member.

* * * * *